United States Patent [19]

Hiramitsu et al.

[11] Patent Number: 5,011,975
[45] Date of Patent: Apr. 30, 1991

[54] (TRANS 1-PROPENYL)DISULFIDE DERIVATIVE AND PROCESS FOR PREPARING THE SAME

[75] Inventors: Tokiyuki Hiramitsu, Kitaibaraki; Ken-ichi Sakamoto, Toyama, both of Japan

[73] Assignee: Nippon Miktron Limited, Tokyo, Japan

[21] Appl. No.: 380,468

[22] Filed: Jul. 17, 1989

[51] Int. Cl.$^5$ .................. C07C 321/00; C07F 7/08; C07F 9/02
[52] U.S. Cl. ........................ 560/147; 556/94; 556/428; 558/104; 562/598; 549/307
[58] Field of Search ............ 556/428, 94; 560/147; 549/307; 558/104; 562/598

[56] References Cited

U.S. PATENT DOCUMENTS 4,438,270  3/1984  Bey et al. .................... 560/167 X

FOREIGN PATENT DOCUMENTS 63-290859  11/1988  Japan .................. 556/428 U X
64-19057   1/1989   Japan .................. 556/428
1117856    5/1989   Japan .................. 556/428

OTHER PUBLICATIONS

Proceedings of AACR, vol. 27, p. 140, Mar. issue, 1986.

Primary Examiner—Paul F. Shaver
Attorney, Agent, or Firm—Fred Philpitt

[57] ABSTRACT

A (trans 1-propenyl)disulfide derivative having a distinguished anti-tumor effect, represented by the following general formula:

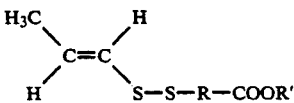

, wherein R is a lower alkylene group and R' is a hydrogen atom or a carboxyl protective group, is prepared by allowing a carboxylic acid thiol derivative, represented by the following general formula:

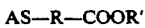

, wherein R and R' have the same meanings as defined above and A is a thiol protective group releasable by a halogenating agent, to react with a trans 1-propenethiol derivative represented by the following general formula:

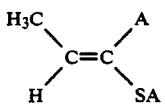

, wherein A has the same meanings as defined above, in the presence of a halogenating agent.

8 Claims, No Drawings

NOVEL (TRANS 1-PROPENYL)DISULFIDE DERIVATIVE AND PROCESS FOR PREPARING THE SAME

BACKGROUND OF THE INVENTION

1. Field of the Invention

This invention relates to a novel (trans 1-propenyl)disulfide derivative and a process for preparing the same, and more particularly to a (trans 1-propenyl)disulfide derivative having a distinguished anti-tumor effect and a process for preparing the same.

2. Description of the Prior Art

Proceedings of AACR, Vol. 27, page 140 (March issue, 1986) discloses a possibility that a propenyl disulfide compound has an anti-cancer effect, but has no clarification of details of the structure of the compound.

SUMMARY OF THE INVENTION

An object of the present invention is to provide a novel propenyl disulfide compound having a distinguished anti-tumor effect.

Another object of the present invention is to provide a process for preparing such a novel propenyl disulfide compound.

DETAILED DESCRIPTION OF THE PREFERRED EMBODIMENTS

The objects of the present invention can be attained by a (trans 1-propenyl)disulfide derivative represented by the following general formula:

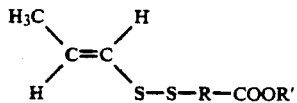 (I)

, wherein R is a lower alkylene group and R' is a hydrogen atom or a carboxyl protective group.

Such a (trans 1-propenyl)disulfide derivative can be prepared by allowing a carboxylic acid thiol derivative represented by the following general formula:

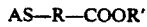 [II]

, wherein R is a lower alkylene group, R' is a hydrogen atom or a carboxyl protective group and A is a thiol protective group, which is releasable by a halogenating agent, to react with a trans 1-propenethiol derivative represented by the following general formula:

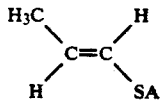 (III)

, wherein A is a thiol protective group, which is releasable by a halogenating agent, in the presence of a halogenating agent according to a process for synthesizing a disulfide compound proposed by the present applicants [Japanese Patent Application Kokai (Laid-open) Nos. 63-290859, 64-19057 and 1-117856].

A carboxylic acid thiol derivative of general formula AS—R—COOH as a starting compound can be derived from a mercapto group-containing lower fatty acid, for example, thioglycolic acid and the carboxylic group may be substituted by a carboxyl protective group.

The carboxyl protective group includes, for example, alkyl groups readily releasable by hydrolysis treatment, such as methyl, ethyl, isopropyl, etc.; ester-forming groups readily releasable by reduction treatment or acid treatment, such as t-butyl, trichloroethyl, methoxymethyl, p-toluenesulfonylethyl, benzyl, 4-nitrobenzyl, diphenylmethyl, trityl, 3,5-di-t-butyl-4-hydroxybenzyl, benzoyloxyethyl, phenacyl, etc.; ester-forming groups readily releasable by in-vivo enzymes such as pivaloyloxymethyl, ethoxycarbonyloxymethyl, phthalidyl, indanyl, etc.; and organic silyl groups, phosphorus groups, tin groups, etc. readily releasable by water or alcohol treatment, such as trimethylsilyl, dimethylsilyl, diethylphosphorus, diethoxyphosphorus, tributyltin, etc.

The thiol protective group of the carboxylic acid thiol derivative and the trans 1-propenethiol derivative that reacts with the carboxylic acid thiol derivative can be removed by a halogenating agent, and includes, for example, substituted or unsubstituted arylalkyl groups such as trityl, diphenylmethyl, benzyl, 4-nitrobenzyl, 4-methoxybenzyl, etc.; substituted or unsubstituted alkyl groups such as benzoyloxyethyl, t-butyl, trichloroethyl, etc.; and alkoxyalkyl groups such as methoxymethyl, etc.

A process for preparing a (trans 1-propenyl)disulfide derivative of general formula [I] by reaction of a starting compound of general formula [II] with another starting compound of general formula [III] will be described below.

A trans 1-propenethiol derivative represented by the general formula [III] and usually about 0.5 to about 1.5 equivalent weights of a carboxylic acid thiol derivative represented by the general formula [II] on the basis of the former are dissolved or suspended in a single solvent inert to the reaction, such as tetrahydrofuran, dioxane, methylene chloride, chloroform, dimethylformamide, acetonitrile, methanol, etc. or a mixture of at least two thereof, and then a capturing agent for a released group is added thereto.

The capturing agent for a released group is a weak nucleophilic agent and includes, for example, reagents having a hydroxyl group such as water, methanol, ethanol, etc. The capturing agent is usually used in large excess of the starting compounds of general formulae [II] and [III] and can be also used as a solvent.

Then, a halogenating agent is added thereto to initiate the reaction. The halogenating agent is a halogen compound capable of supplying a positively charged halogen atom such as Cl+, Br+, I+, etc., usually known as a positively charged halogen supply source, and includes, for example, halogens such as chlorine, bromine, iodine, etc.; N-haloimides such as N-chlorosuccinimide, N-bromosuccinimide, N-iodosuccinimide, etc.; N-halosulfoneamides such as N-chlorobenzenesulfoneamide, N-chloro-p-toluenesulfoneamide, etc.; 1-halobenztriazoles: organic hypohalogenides such as t-butyl hypochloride, t-butyl hypoiodide, etc.; N,N'-dibromohydantoin, etc.

The halogenating agent is used in a sufficient amount for supplying an equivalent weight of halogen to the starting compounds of general formulae [II] and [III], usually about 2 to about 6 equivalent weights on the basis of the starting compounds of general formula [II]. After the completion of the reaction, the halogenating agent in excess is removed by treatment with such a weak reducing agent as not to break the disulfide bond. The reducing agent includes, for example, sodium sulfite, sodium hydrogen sulfite, sodium thiosulfate, phosphorous acid triester, etc.

The reaction is carried out at a temperature of usually about 0° to about 100° C., preferably about 0° to about 30° C., for a reaction time of about 0.5 to about 4 hours. The reaction is then discontinued by adding a reducing agent to the reaction system.

The thus obtained (trans 1-propenyl)disulfide derivative of general formula [I] can be separated from the reaction mixture according to a conventional procedure. The reaction product of general formula [I] completely retains a steric configuration of the starting compound of general formula [III].

According to the present invention, a (trans 1-propenyl)disulfide derivative having a distinguished anti-tumor effect can be provided as a novel compound.

PREFERRED EMBODIMENTS OF THE INVENTION

The present invention will be described in detail below, referring to Examples and Reference Examples.

REFERENCE EXAMPLE 1

48 ml of allylmercaptan and 129.6 g of trityl alcohol were suspended in 500 ml of acetic acid and 2.0 ml of concentrated sulfuric acid was dropwise added thereto at room temperature with stirring. Then, the mixture was further stirred for one hour under the same conditions as above, and the precipitates were recovered therefrom by filtration, washed with 200 ml of methanol and then thoroughly washed with water. The resulting colorless powder was dissolved in benzene, washed with an aqueous 5% sodium hydrogen carbonate solution and then with water, and dried over anhydrous magnesium sulfate, and the solvent was removed therefrom by distillation under reduced pressure. The residue was treated with a small amount of methanol to obtain 130 g of allyl tritylsulfide (melting point: 99°–101° C.).

Then, 12.64 g of allyl tritylsulfide was dissolved in a solvent mixture consisting of 130 ml of t-butanol and 70 ml of tetrahydrofuran, and 9.0 g of pottasium tert.-butoxide was added to the resulting solution at room temperature with stirring, and the mixture was further stirred for 15 hours. The solvents were removed from the reaction mixture at a temperature of below 40° C. by distillation under reduced pressure, and then 200 ml of water and 400 ml of benzene were added to the residue to extract. The benzene layer was washed with water and dried over anhydrous magnesium sulfate. Then, the solvent was removed therefrom by distillation under reduced pressure. The residue was subjected to silica gel column chromatography and eluted with n-hexane, whereby 5.0 g of trans 1-propenyl tritylsulfide (melting point: 105°–106° C.) was obtained as colorless crystal.

Elemental analysis (as $C_{22}H_{20}S$): Calculated: C: 83.50%, H: 6.37%; Found: C: 83.75%, H: 6.10%.

NMR (CDCl$_3$, ppm): 1.58 (3H, dd J=6 Hz and 1 Hz, CH$_3$),

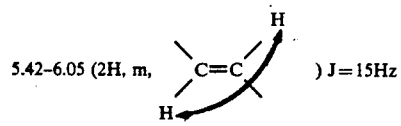
5.42–6.05 (2H, m, \C=C/ ) J=15Hz 7.15–7.40 (15H, m, aromatic H̲).

REFERENCE EXAMPLE 2

0.3 ml of concentrated sulfuric acid was dropwise added to a solution consisting of 9.2 g of thioglycolic acid HSCH$_2$COOH, 26.0 g of trityl alcohol (C$_6$H$_5$)$_3$COH and 50 ml of acetic acid at room temperature with stirring, and the resulting mixture was further stirred for one hour. Then, the reaction mixture was poured into ice-water and the precipitates were recovered therefrom by filtration, washed with water and dried, whereby 31.7 g of colorless, powdery carboxymethyl tritylsulfide (C$_6$H$_5$)$_3$CSCH$_2$COOH was obtained (yield: 95%).

NMR (CDCl$_3$, ppm): 2.77 (2H, s, SCH̲$_2$), 6.40–7.10 (15H, m, aromatic H̲).

REFERENCE EXAMPLE 3

0.6 ml of concentrated sulfuric acid was dropwise added to a solution consisting of 10.6 g of β-mercaptopropionic acid HSCH$_2$CH$_2$COOH, 26.0 g of trityl alcohol and 150 ml of acetic acid at room temperature with stirring, and the resulting mixture was further stirred for one hour. Then, the precipitates were recovered therefrom by filtration, washed with acetic acid and dried, whereby 25 g of colorless, powdery 2-carboxyethyl tritylsulfide (C$_6$H$_5$)$_3$CSCH$_2$CH$_2$COOH was obtained.

NMR (CDCl$_3$, ppm): 2.2–2.6 (4H, m, CH̲$_2$CH̲$_2$), 7.15–7.55 (15H, m, aromatic H̲).

REFERENCE EXAMPLE 4

0.6 ml of concentrated sulfuric acid was dropwise added to a solution consisting of 10.6 g of thiolactic acid HSCH(CH$_3$)COOH, 26.0 g of trityl alcohol and 100 ml of acetic acid at room temperature with stirring, and the resulting mixture was further stirred for 3 hours. Then, the reaction mixture was poured into ice-water, and the precipitates were recovered therefrom by filtration, washed with water and further with a small amount of methanol, and dried, whereby 31.4 g of colorless, powdery 1-carboxyethyl tritylsulfide (C$_6$H$_5$)$_3$CSCH(CH$_3$)COOH was obtained.

NMR (CDCl$_3$, ppm): 1.21 (3H, d J=7.3 Hz, CHCH̲$_3$), 3.03 (1H, q J=7.3 Hz, CH̲CH$_3$), 7.2–7.50 (15H, m, aromatic H̲).

REFERENCE EXAMPLE 5

0.6 ml of concentrated sulfuric acid was dropwise added to a solution consisting of 12.2 g of ethyl thioglycolate HSCH$_2$COOC$_2$H$_5$, 26.0 g of trityl alcohol and 100 ml of acetic acid at room temperature with stirring, and the resulting mixture was further stirred for 3 hours. Then, the reaction mixture was poured into ice-water, and then the precipitates were recovered therefrom by filtration, washed with water, and dried, whereby 35 g of colorless, powdery ethoxycarbonylmethyl tritylsulfide (C$_6$H$_5$)$_3$CSCH$_2$COOC$_2$H$_5$ was obtained.

NMR (CDCl$_3$, ppm): 1.19 (3H, t J=7.5 Hz, CH$_2$CH̲$_3$), 2.96 (2H, s, SCH̲$_2$CO), 4.05 (2H, q J=7.5 Hz, CH̲$_2$CH$_3$), 7.10–7.52 (15H, m, aromatic H̲).

EXAMPLE 1

10 ml of water and 2.54 g of iodine were added to a solution consisting of 3.16 g of trans 1-propenyl tritylsulfide obtained in Reference Example 1, 3.34 g of carboxymethyl tritylsulfide obtained in Reference Example 2 and 50 ml of tetrahydrofuran at room temperature with stirring, and the resulting mixture was further stirred for 3 hours. Then, 2.54 g of sodium sulfite was added thereto, and the mixture was stirred until the reaction mixture turned yellow.

After the completion of the reaction, ethyl acetate and water were added to the reaction mixture to extract, and the ethyl acetate layer was washed with water, dried over anhydrous magnesium sulfate and then concentrated to dryness at a temperature of below 20° C. The residue was subjected to silica gel chromatography, whereby 170 mg of colorless or light yellowish, oily carboxymethyl (trans 1-propenyl)disulfide $CH_3CH=CHSSCH_2COOH$ was obtained.

Elemental analysis (as $C_5H_8O_2S_2$): Calculated: C: 36.56%, H: 4.91%; Found: C: 36.27%, H: 5.02%.

NMR ($CDCl_3$, ppm): 1.78 (3H, d J=2.5 Hz, $CH_3$), 3.48 (2H, s, $CH_2$), 5.80–6.25 (2H, m, vinyl position $\underline{H}$), 7.60 (1H, b, $C\overline{O_2}H$).

Mass spectrum: (70 eV): M/e (relative intensity): 166(M$^+$+2, 3), 164(M$^+$, 31), 119(6), 105(14), 73(29), 72(44), 62(15), 47(100).

EXAMPLE 2

20 ml of water and 10.16 g of iodine were added to a solution consisting of 6.32 g of trans 1-propenyl tritylsulfide obtained in Reference Example 1, 6.96 g of 2-carboxyethyl tritylsulfide obtained in Reference Example 3 and 100 ml of tetrahydrofuran at room temperature with stirring, and the resulting mixture was further stirred for 3 hours. Then, 10.16 g of sodium sulfite and 100 ml of water were added thereto, and the mixture was stirred until the reaction mixture turned yellow.

After the completion of the reaction, ethyl acetate and water were added to the reaction mixture to extract, and the ethyl acetate layer was washed with water, dried over anhydrous magnesium sulfate and concentrated to dryness at a temperature of below 20° C. The residue was subjected to silica gel chromatography, whereby 720 mg of 2-carboxyethyl (trans 1-propenyl)disulfide $CH_3CH=CHSSCH_2CH_2COOH$ (melting point: 35°–42° C.) was obtained.

Elemental analysis (as $C_6H_{10}O_2S_2$): Calculated: C: 40.42%, H: 5.65%; Found: C: 40.63%, H: 5.50%.

NMR ($CDCl_3$, ppm): 1.78 (3H, d J=5.5 Hz, $CH_3$), 2.70–2.98 (4H, m, $\underline{CH_2}CH_3$), 5.80–6.25 (2H, m, vinyl position H).

Mass spectrum: (70 eV): M/e (relative intensity): 180(M$^+$+2, 8), 178(M$^+$, 85), 105(21), 74(80), 73(50), 72(52), 62(23), 56(21), 47(100).

EXAMPLE 3

15 ml of water and 15.24 g of iodine were added to a solution consisting of 9.48 g of trans 1-propenyl tritylsulfide obtained in Reference Example 1, 10.44 g of 1-carboxyethyl tritylsulfide obtained in Reference Example 4 and 120 ml of tetrahydrofuran at room temperatue with stirring, and the resulting mixture was further stirred for 2 hours. Then, 15.3 g of sodium sulfite and 40 ml of water were added thereto, and the reaction mixture was stirred until it turned yellow.

After the completion of the reaction, ethyl acetate and water were added to the reaction mixture to extract, and the ethyl acetate layer was washed with water, dried over anhydrous magnesium sulfate and concentrated to dryness at a temperature of below 20° C. The residue was subjected to silica gel chromatography, whereby 1.2 g of colorless or light yellowish oily 1-carboxyethyl (trans 1-propenyl)disulfide $CH_3CH=CHSSCH(CH_3)COOH$ was obtained.

Elemental analysis (as $C_6H_{10}O_2S_2$): Calculated: C: 40.42%, H: 5.65%; Found: C: 40.40% H: 5.52%.

NMR ($CDCl_3$, ppm): 1.53 (3H, d J=7.3 Hz, $C\underline{H}(CH_3)COOH$), 1.77 (3H, d J=5.1 Hz, $CH_3C\underline{H}=CH$), 3.58 (1H, q J=7.3 Hz, $C\underline{H}(CH_3)COOH$), 5.90–6.2 (2H, m, vinyl position $\underline{H}$).

Mass spectrum: (70 eV): M/e (relative intensity): 180 (M$^+$+2, 10), 178(M$^+$, 100), 106(30), 105(95), 74(63), 73(75), 72(77), 61(74), 59(48).

EXAMPLE 4

12 ml of water and 10.16 g of iodine were added to a solution consisting of 6.32 g of trans 1-propenyl tritylsulfide obtained in Reference Example 1, 7.24 g of ethoxycarbonylmethyl tritylsulfide obtained in Reference Example 5 and 80 ml of tetrahydrofuran at room temperature with stirring, and the resulting mixture was further stirred for 1.5 hours. Then, 10.16 g of sodium sulfite and 15 ml of water were added thereto, and the reaction mixture was stirred until it turned yellow.

After the completion of reaction, ethyl acetate and water were added to the reaction mixture to extract, and the ethyl acetate layer was washed with water, dried over anhydrous magnesium sulfate and concentrated to dryness at a temperature of below 20° C. The residue was subjected to silica gel chromatography, whereby 0.8 g of colorless or light yellowish oily ethoxycarbonylmethyl (trans 1-propenyl)disulfide $CH_3CH=CHSSCH_2COOC_2H_5$ was obtained.

Elemental analysis (as $C_7H_{12}O_2S_2$): Calculated: C: 43.72%, H: 6.29%; Found: C: 43.56%, H: 6.41%.

NMR ($CDCl_3$, ppm): 1.30 (3H, t J=7.2 Hz, $CH_2C\underline{H_3}$), 1.77 (3H, d J=5.2 Hz, $CH_3C\underline{H}=CH$), 3.46 (2H, s, $SCH_2$), 4.20 (2H, q J=7.2 Hz, $C\underline{H_2}CH_3$), 5.8–6.2 (2H, m, vinyl position $\underline{H}$).

Mass spectrum: (70 eV): M/e (relative intensity); 194(M$^+$+2, 8), 192(M$^+$, 79), 119(30), 105(28), 74(39), 73(86), 72(93), 62(21), 49(25), 47(100).

TESTS ON ANTI-TUMOR EFFECT

Test 1

Six to eight week-old male ICR mice inoculated SC $10^6$ cells of Ehrlich ascites tumor were injected intratumorally with 33 mg/kg of the disulfide compound (Example 1) which was suspended in saline containing 2% ethanol from day 0 to day 6. Control group were injected with only the solvent by the same way. The tumor size was measured weekly and tumor weight was calculated using the following formula:

Tumor weight (26mg) = [major axis × (minor axis)$^2$]/2.

The average tumor weights of each group on day 21 were 5.1±0.72 g (control) and 3.0±0.64 g (experimental group, P<0.05), respectively.

Test 2

ICR mice transplanted ip $10^5$ cells of Ehrlich ascites tumor were daily given ip 33 mg/kg of tested sample (Example 1) from day 0 for day 7 days. The control group died from day 11 to day 22 and the average survival time was 16.1±1.0 days. The tested group died from day 16 to day 31 and the average survival time was 22.1±1.5.

Test 3

When mice inoculated ip $10^5$ cells of Ehrlich ascites tumor were daily injected ip with 33 mg/kg of the sample (Example 2) dissolved in suqualene from day 0 for day 7 days, the survival times were from 13 days to 32 days and from 11 days to 18 days in the tested group and in control group, respectively, and the average survival times were 21.7±1.7 days and 15.7±0.6, respectively.

What is claimed is:

1. A process for preparing a (trans 1-propenyl)disulfide derivative represented by the following general formula:

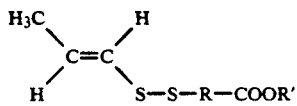
(I)

, wherein R is a lower alkylene group and R' is a hydrogen atom or a carboxyl protective group, which comprises allowing a carboxylic acid thiol derivative represented by the following general formula:

AS—R—COOR'  [II]

, wherein R and R' have the same meanings as defined above and A is a thiol protective group releasable by a halogenating agent, to react with a trans 1-propenethiol derivative represented by the following general formula:

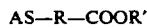
(III)

, wherein A has the same meanings as defined above, in the presence of a halogenating agent.

2. A process according to claim 1, wherein the lower alkylene group is —CH$_2$—, —CH$_2$CH$_2$— or —CH(CH$_3$)— group.

3. A process according to claim 1, wherein the carboxyl protective group is an alkyl group readily releasable by hydrolysis, an ester-forming group readily releasable by reduction treatment or acid treatment, an ester-forming group readily releasable by an in-vivo enzyme, or an organic silyl group, phosphorus group or tin group readily releasable by water or alcohol treatment.

4. A process according to claim 1, wherein the protective group releasable by a halogenating agent is a substituted or unsubstituted arylalkyl group, a substituted or unsubstituted alkyl group or an alkoxyalkyl group.

5. A process according to claim 1, wherein the reaction is carried out in the presence of a capturing agent for a released group.

6. A process according to claim 5, wherein the capturing agent for a released group is a hydroxyl group-containing compound.

7. A process according to claim 1, wherein the halogenating agent is a compound capable of supplying a positively charged halogen atom.

8. A process according to claim 1, wherein after the completion of the reaction the halogenating agent used in excess is removed by treatment with such a weak reducing agent as not to break a disulfide bond.

* * * * *